United States Patent
Hondo et al.

(10) Patent No.: US 7,202,471 B2
(45) Date of Patent: Apr. 10, 2007

(54) METHOD AND APPARATUS FOR MASS SPECTROMETRY

(75) Inventors: Toshinobu Hondo, Tokyo (JP); Jun Tamura, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 11/284,144

(22) Filed: Nov. 21, 2005

(65) Prior Publication Data

US 2006/0145070 A1    Jul. 6, 2006

(30) Foreign Application Priority Data

Nov. 30, 2004   (JP) .............................. 2004-345650

(51) Int. Cl.
*H01J 49/00*  (2006.01)

(52) U.S. Cl. ..................... 250/281; 250/282; 73/53.01; 702/22; 702/30; 210/656

(58) Field of Classification Search ................ 250/281, 250/282; 73/23.22, 53.01; 702/19, 22, 23, 702/27, 30, 32; 210/656, 198.2; 436/173
See application file for complete search history.

(56) References Cited

U.S. PATENT DOCUMENTS 6,369,382 B1 *  4/2002  Ito et al. ...................... 250/281
6,573,492 B2 *  6/2003  Nagai .......................... 250/282

FOREIGN PATENT DOCUMENTS

JP      01-118763     5/1989
JP      2001-050945   2/2001

* cited by examiner

*Primary Examiner*—Kiet T. Nguyen
(74) *Attorney, Agent, or Firm*—The Webb Law Firm

(57) ABSTRACT

A method of mass spectrometry. The method starts with gaining a total ion chromatogram by a mass spectrometer. An accumulation mass spectrum indicating vicinities of a desired peak top of the total ion chromatogram is displayed. The operator selects a desired mass peak from the displayed accumulation mass spectrum. Another mass chromatogram that is coincident in elution start time, maximum elution time, and elution end time with the mass chromatogram of the selected mass peak are extracted and selected out as a mass peak. Thus, a mass spectrum of a single component is reconstructed.

18 Claims, 4 Drawing Sheets

MASS CHROMATOGRAM

METHOD AND APPARATUS FOR MASS SPECTROMETRY

BACKGROUND OF THE INVENTION

1. Field of the Invention

The present invention relates to apparatus and method for mass spectrometry for quickly performing qualitative and quantitative analyses of quite complex sample mixtures typified by peptide mixtures obtained by enzymatic digestion of proteins.

2. Description of Related Art

In recent years, proteins have been identified by comparing mass spectra of proteins or peptides obtained by enzymatic digestion of proteins against a database or library of information about known amino acid sequences of proteins (molecular structures). Peptide mixtures obtained by enzymatically digesting and fractionating proteins include tens of kinds of peptides. It is regarded as important that accurate mass spectral information about at least several kinds of peptides be obtained, in order to precisely identify peptides.

Liquid chromatography is widely used to separate and analyze various components of samples/solutions, such as peptide mixtures. Such a liquid chromatograph is made up of a sample-separating portion and a chromatogram-measuring portion. The sample-separating portion includes a pump, an injector, and a column. A mixture sample consisting of plural components is separated into the components by the sample-separating portion. The process of elution is measured by a mass spectrometer. A mass spectrum of each isolated component can be obtained. See Japanese Patent Laid-Open No. 2001-50945 and Japanese Patent Laid-Open No. H1-118763.

However, with the existing liquid chromatograph, it is often quite difficult to completely separate plural components in a single chromatographic run. Especially, in order to completely isolate naturally occurring samples, such as digestive products enzymatically derived from proteins, it is necessary to discuss the separation conditions of the liquid chromatograph according to each sample, thus requiring much labor and time.

In addition, even if a lot of labor and time are spent, components of interest cannot be isolated in many cases. It has been quite difficult to obtain a mass spectrum of each component using an easy method.

As an example, FIG. 1 shows an enlargement of a part of a mass chromatogram of a peptide mixture obtained by enzymatically digesting fetal bovine serum albumin with trypsin. The solid line indicates the total ion chromatogram. The broken line indicates a chromatogram obtained at m/z=1479.43. The dot-and-dash line indicates a chromatogram obtained at m/z=966.474.

As is obvious from the diagram, with respect to a peak with 36.65 min, at least two different components are eluted. Any region of the peaks which is sufficiently isolated to produce a pure spectrum hardly exists.

In this case, with the prior art technique, any one of the following methods has been used to obtain a separate mass spectrum of each component:

(1) The components are separated after rediscussing the separation conditions.

(2) MS/MS is used.

However, a lot of time, labor, and skillfulness are required to rediscuss the separation conditions. Furthermore, in the case of complex mixtures, such as protein decomposition products, it is customary that not all components can be separated in one chromatographic step.

In the method using MS/MS, substances of interest are selectively isolated using a mass spectrometer after chromatographic separation. Then, a mass spectrum is obtained and so it is possible to quickly solve the foregoing problem. However, a MS/MS instrument is generally expensive. Furthermore, complex manipulations are required. Consequently, there is a demand for an easy and inexpensive method.

SUMMARY OF THE INVENTION

In view of the foregoing circumstances, it is an object of the present invention to provide method and apparatus for mass spectrometry capable of separating each component of a complex structure that would not be normally easily separated, such as digestive products enzymatically derived from proteins, and thus capable of producing a mass spectrum of each component.

This object is achieved by a method of mass spectrometry in accordance with the present invention, the method comprising the steps of: separating a mixture into components by a chromatograph; ionizing the separated mixture components, obtaining measurement data from a mass spectrometer; producing a mass chromatogram from the obtained measurement data for a given period; extracting a spectrum from the mass chromatogram; and searching a library holding information about molecular structures of known compounds to thereby perform a qualitative or quantitative analysis of a compound. A total ion chromatogram is obtained from the mass spectrometer. An accumulation mass spectrum close to desired peak tops is extracted from the total ion chromatogram and displayed. A desired mass peak is selected from the displayed accumulation mass spectrum. Another mass chromatogram that is coincident in elution start time, maximum elution time, and elution end time with the mass chromatogram of the selected mass peak is extracted. This is selected out as a mass peak. In this way, a mass spectrum of a single component is reconstructed.

In one feature of the method, the determination of the elution start time from the chromatograph, maximum elution time, and elution end time is done by fitting of a curve of a given function to the time variation of the mass chromatogram.

In another feature of the method, the curve of the given function is a curve of a higher-order function or Gaussian function.

In a further feature of the method, the chromatograph is a liquid chromatograph.

In yet another feature of the method, the mixture is a peptide mixture obtained by enzymatic digestion of a protein.

The present invention further provides a method of mass spectrometry for performing a qualitative or quantitative analysis of a compound by isolating a mixture into components by a chromatograph, ionizing the mixture components, obtaining measurement data from a mass spectrometer for a given period, storing the obtained measurement data in a storage device, extracting a spectrum based on the stored mass spectra, and searching a library holding information about molecular structures of known compounds. This method of mass spectrometry is characterized as follows. Mass peaks producing chromatograms which are coincident in waveform with the mass chromatogram of a mass peak having a given peak intensity are found from a storage area storing all detected mass chromatograms and taken as a chromatogram group. This operation is repeated to isolate and reconstruct each molecular ion peak and a fragment spectrum of a single component corresponding to the peak.

In one feature of this method, the mass peak having the given peak intensity is a mass peak having the highest intensity out of mass peaks not yet contained in the group.

In another feature of this method, the decision as to whether the chromatogram is coincident in waveform with the mass chromatogram of a mass peak having a given peak intensity is made by comparisons in terms of elution start time from the chromatograph, maximum elution time, and elution end time.

In still another feature of this method, the determination of the elution start time from the chromatograph, maximum elution time, and elution end time is done by fitting of a curve of a given function to the time variation of the mass chromatogram.

In yet another feature of this method, the curve of the given function is a curve of a higher-order function or Gaussian function.

In a further feature of this method, the chromatograph is a liquid chromatograph.

In yet another feature of this method, the mixture is a peptide mixture obtained by enzymatic digestion of a protein.

Furthermore, the present invention provides a mass spectrometry apparatus for performing a qualitative or quantitative analysis of a compound by isolating a mixture into components by a chromatograph, ionizing the mixture components, obtaining measurement data from a mass spectrometer for a given period, obtaining a mass chromatogram from the obtained measurement data, extracting a spectrum from the mass spectrogram, and searching a library holding information about molecular structures of known compounds. The mass spectrometry apparatus comprises: a display means for displaying an accumulation mass spectrum close to a desired peak top from a total ion chromatogram gained by the mass spectrometer; a selection means for selecting a desired mass peak from the displayed accumulation mass spectrum; and a reconstruction means for reconstructing a mass spectrum of a single component by extracting other mass chromatogram that is coincident in elution start time, maximum elution time, and elution end time with the mass chromatogram of the selected mass peak and selecting out the extracted mass chromatogram as a mass peak.

In one feature of this mass spectrometer, the determination of the elution start time from the chromatograph, maximum elution time, and elution end time is done by fitting of a curve of a given function to the time variation of the mass chromatogram.

In another feature of this mass spectrometry apparatus, the curve of the given function is a curve of a higher-order function or Gaussian function.

In a further feature of this mass spectrometry apparatus, the chromatograph is a liquid chromatograph.

In yet another feature of this mass spectrometry apparatus, the mixture is a peptide mixture obtained by enzymatic digestion of a protein.

In addition, in the present invention, any one of the above-described methods of mass spectrometry is applied to plural mass chromatograms measured in a multifunctional mode under different mass spectrometry conditions. Thus, each molecular ion peak and a fragment spectrum of a single component corresponding to the peak are reconstructed.

According to the method and apparatus for mass spectrometry of the present invention, a mixture is isolated into components by a chromatograph. The isolated mixture components are ionized. Measurement data are obtained for a given period by a mass spectrometer. A spectrum is extracted from a mass chromatogram indicated by the gained measurement data. A library holding spectra of known compounds is searched. Thus, a qualitative or quantitative analysis of a compound is performed. Mass chromatograms that are coincident in elution start time from the chromatograph, maximum elution time, and elution end time are extracted from the mass chromatograms of gained mass peaks. The selected chromatograms are selected out as mass peaks. In this way, a mass spectrum of a single component is reconstructed. The determination of the elution start time from the chromatograph, maximum elution time, and elution end time is done by fitting of a curve of a higher-order function or Gaussian function to the time variation of the mass chromatogram. Consequently, a mass spectrum of each component of a mixture that is complex and difficult to isolate into components, such as digestive products enzymatically derived from proteins, can be obtained by an isolation technique.

Other objects and features of the invention will appear in the course of the description thereof, which follows.

DESCRIPTION OF THE PREFERRED EMBODIMENTS

The preferred embodiments of the present invention are hereinafter described with reference to the accompanying drawings.

Embodiment 1

Figure 1:
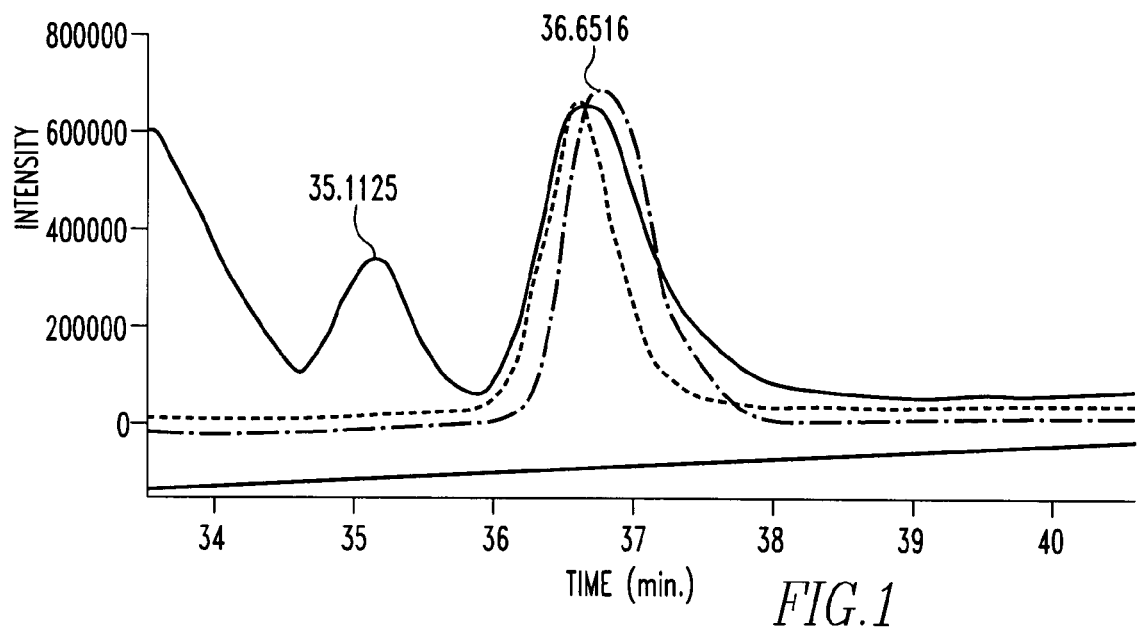
FIG. 1 is a mass chromatogram of a peptide mixture obtained by enzymatically digesting fetal bovine serum albumin with trypsin.
Figure 2:
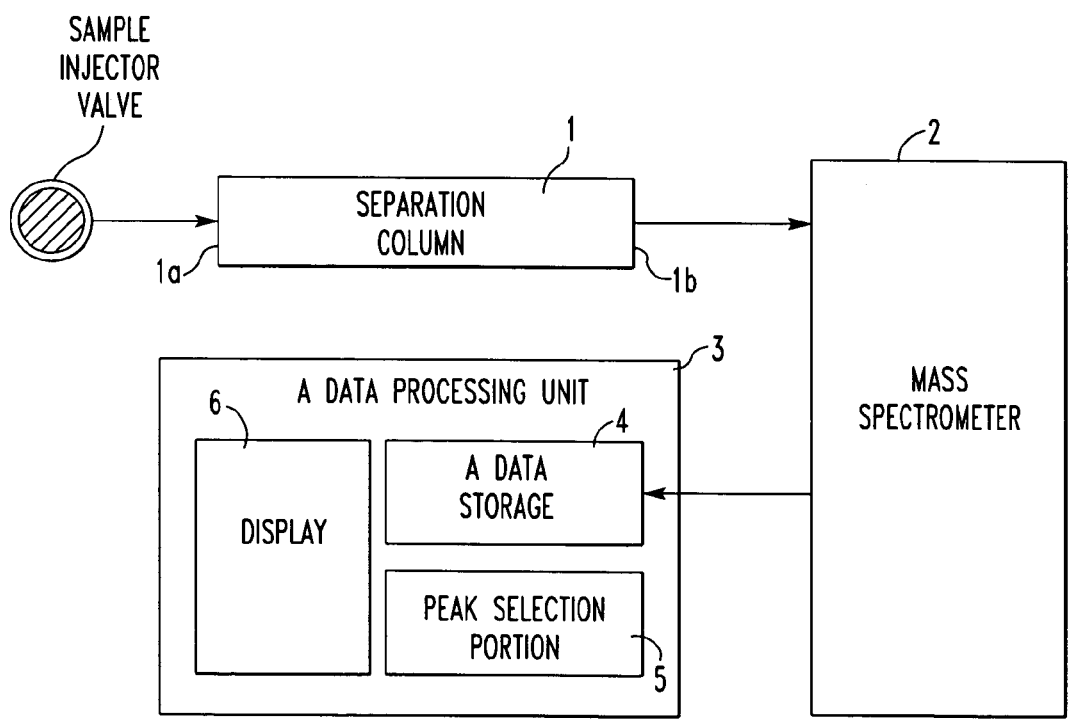
FIG. 2 is a diagram showing a liquid chromatograph-mass spectrometer system according to the present invention.

FIG. 2 illustrates apparatus and method for mass spectrometry according to the present invention. The structures of main portions of a liquid chromatograph-mass spectrometer system used in the present invention are shown in FIG. 2.

In FIG. 2, a separation column 1 has an inflow end 1a into which a liquid sample containing plural components is supplied. The column also includes an exit end 1b from which an eluate including the separated components flows. A mass spectrometer 2 is equipped downstream of the exit end 1b.

A spectrum obtained from the mass spectrometer 2 is analyzed by a data processing unit 3, which has a data storage 4, a peak selection portion 5, and a display 6. The data storage 4 consists, for example, of a hard disk and stores spectral data sent from the mass spectrometer 2 at each timing. The peak selection portion 5 consists of a display device for displaying a mass chromatogram and an input device for selecting a mass peak, such as a mouse. The peak selection portion 5 permits selection of mass peaks having different mass numbers.

Figure 3A:
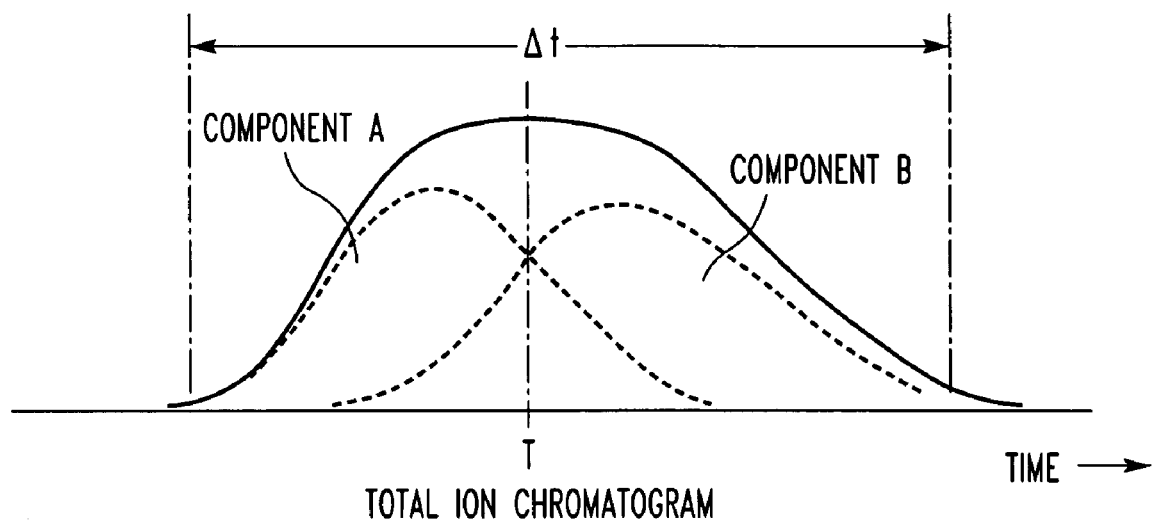
FIGS. 3A to 3D show graphs illustrating one example of method of mass spectrometry according to the present invention.

The operation of the data processing unit 3 is described with reference to FIGS. 3A to 3D. First, the data processing unit 3 displays vicinities of a given peak top T selected by the human operator from a total ion chromatogram. This is shown in FIG. 3A. It is assumed here that components A and B are overlapped in the eluate.

Figure 3B:
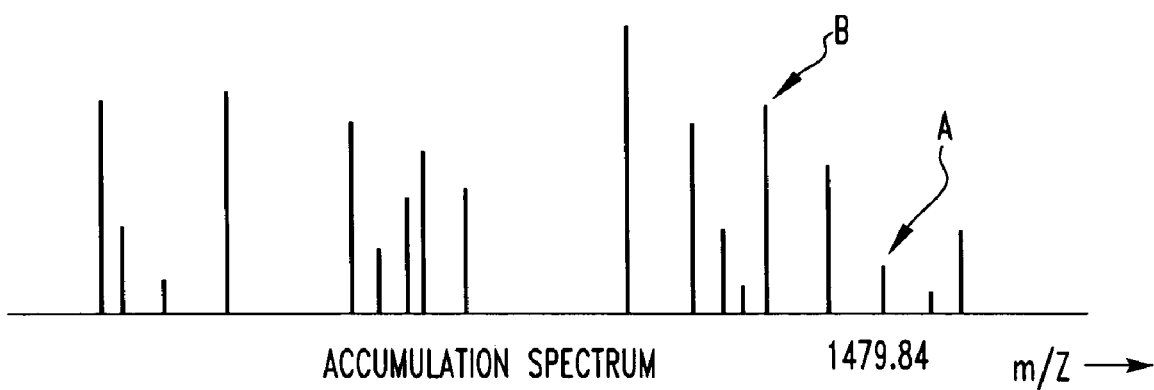

Then, a given time interval Δt around the peak top T is specified by the operator. An accumulation spectrum (S) in the time interval Δt is displayed. This is shown in FIG. 3B.

The operator then selects an arbitrary mass number (A) of interest on the mass spectrum (S). Where data are measured in a multifunctional mode, the mass peak at the mass number (A) (e.g., m/z=1479.84) at a mass chromatogram measured under mass spectrometry conditions which are empirically found to produce the least fragmentation is specified. In the multifunctional mode, mass spectra are gained simultaneously at different ionization voltages by switching ionization voltage measurement conditions between plural different conditions at a high speed in one chromatographic analysis.

Figure 3C:
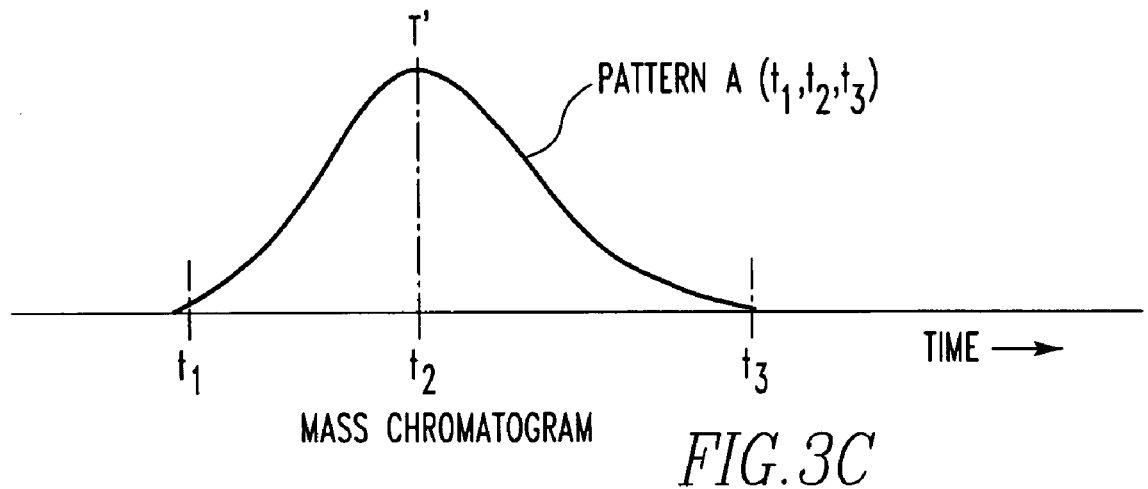

The data processing unit 3 processes the selected mass peak (A) in the manner described below. First, a mass chromatogram extending in time, for example, about 10σ (where σ is the standard deviation of the spread of the peak in time from the center of the peak of the mass chromatogram) forward and rearward from the center T' of the peak of the mass chromatogram drawn by the mass peak (A) to be processed is read from the data storage 4. This is shown in FIG. 3C.

Then, the elution curve of the mass chromatogram created regarding the mass peak (A) is characterized. Curves of higher-order functions, such as quadratic curves or curves of Gaussian functions, are fitted to the waveform of the obtained chromatogram. Using this curve fitting method, the values of the elution start time $t_1$ of the elution component giving rise to the mass peak from the separation column, maximum elution time $t_2$, and elution end time $t_3$ are estimated at high accuracy. The width of the peak (e.g., the width of 4σ) is calculated.

Then, the values of the elution start time $t_4$ of each mass peak (e.g., mass peak (B)) corresponding to each mass number on the accumulation spectrum (S) from the separation column, maximum elution time $t_5$, and elution end time $t_6$ are found by a method similar to the method using mass chromatograms. These are compared with the elution start time $t_1$, maximum elution time $t_2$, and elution end time $t_3$ of the mass chromatogram of the mass number (A) specified by the operator. Only the mass numbers of mass peaks lying within a tolerable range of values (i.e., not exceeding preset threshold values) are temporarily stored.

Figure 3D:
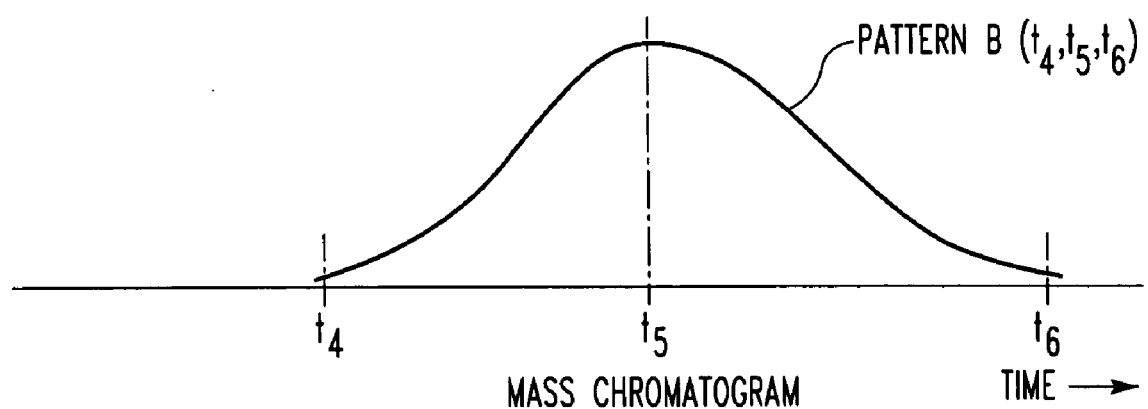

Consequently, only mass peaks showing the same elution curve pattern can be selected out. In the case of the mass peak (B), the pattern of the elution curve is different and so the mass number of this mass peak is not stored. This is shown in FIG. 3D.

Figure 4A:
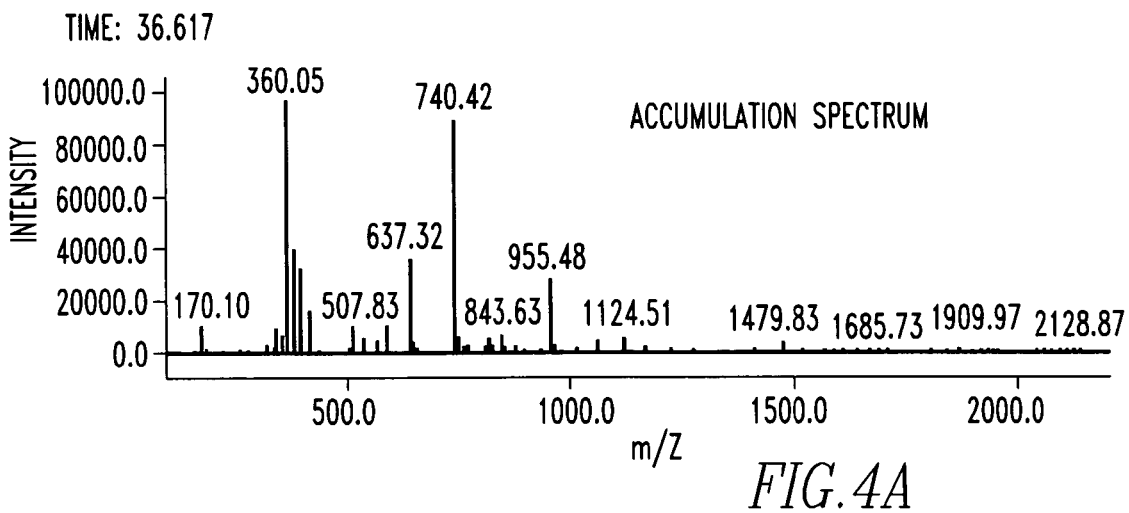
FIGS. 4A to 4C are mass spectra obtained by a method of mass spectrometry according to the present invention.
Figure 4B:
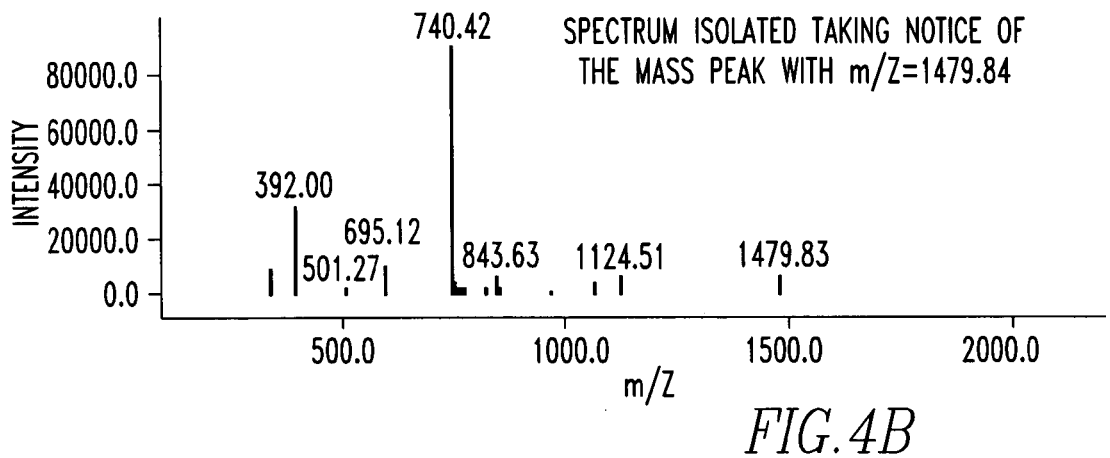

Finally, mass peaks not coincident with the mass numbers temporarily stored by the aforementioned data processing operations are excluded from the mass peaks within the accumulation spectrum (S) shown in FIG. 4A. As a result, a pure mass spectrum of a substance corresponding to the mass number (A) selected by the operator can be obtained. The results are output from the display 6.

Figure 4C:
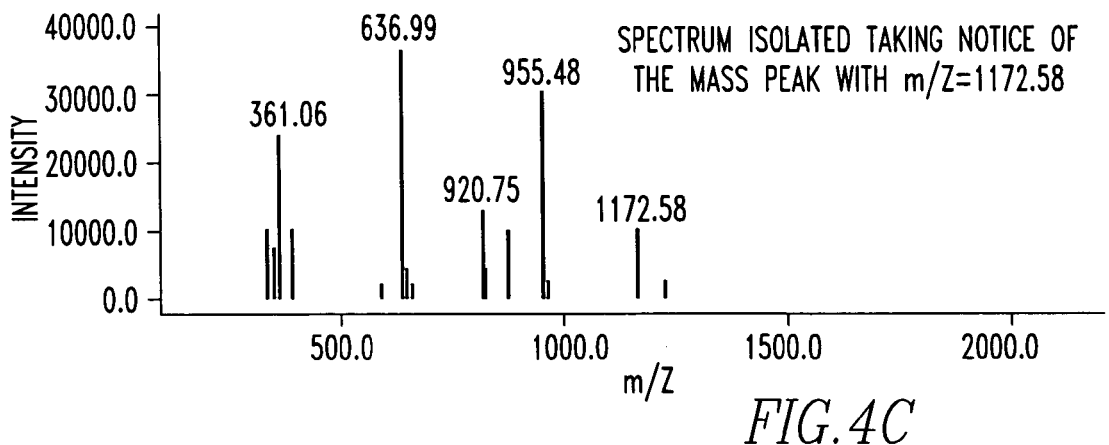

A spectrum isolated while taking notice of the values of the elution start time, maximum elution time, and elution end time of the mass chromatogram drawn by the mass peak with m/z=1479.84 by the above-described method is shown in FIG. 4C.

Where data are measured in the multifunctional mode, data about the other ionization voltages stored are similarly processed. Mass peaks which produce mass chromatograms coincident in elution start time, maximum elution time, and elution end time are extracted from mass spectra (mass spectra producing fragmentation) of other ionization voltages corresponding to the initially output accumulation spectrum (S), and the results are output from the display 6.

Embodiment 2

Other apparatus and method for mass spectrometry according to the present invention are described below. The main portions of the liquid chromatograph-mass spectrometer system are similar in structure to the system of Embodiment 1 already described in connection with FIG. 2.

In the present embodiment, the data processing unit 3 first creates an accumulation spectrum (S) in a time interval corresponding to a time width, for example, of 3σ or 4σ of a given peak on a total ion chromatogram selected by the operator and temporarily stores it in a first storage area (M) of the data storage 4.

The data processing unit 3 then internally creates mass chromatograms corresponding to all the mass peaks on the accumulation spectrum (S) within time intervals, for example, of 10σ before and after the selected total ion chromatogram peak and detects mass chromatogram peaks.

Then, curves of high-order functions, such as quadratic curves or curves of Gaussian functions, are fitted to the waveforms of all the detected mass chromatogram peaks. Where the chromatogram peak width is assumed to be 4σ, for example, the maximum elution time, elution start time, and elution end time are estimated at high accuracy by this curve fitting method.

Then, all the obtained mass peaks are arrayed in turn from the highest peak intensity. Mass peaks having the same pattern of elution curve as the pattern of elution curve of the mass peak (P1) of the highest intensity are extracted by referring to their values of the maximum elution time, elution start time, and elution end time. These spectra are removed from the first storage area (M) of the data storage 4. The extracted results are stored in a second storage area (M1).

Then, mass peaks having the same pattern of elution curve as the pattern of elution curve of the peak (P2) of the highest intensity are extracted from the remaining mass peaks held in the first storage area (M) of the data storage 4 by referring to their values of the maximum elution time, elution start time, and elution end time. The extracted peaks are deleted from the first storage area (M) of the data storage 4. The extracted results are stored in a third storage area (M2).

The processing described so far is repeated until the first storage area (M) of the data storage 4 becomes empty. Thus, (M1), (M2), . . . , (Mn) are derived.

Only a mass peak that is coincident in mass number with the peak stored in the second storage area (M1) is extracted from the accumulation spectrum (S) obtained first. This extracted peak is taken as a spectrum (S1). Similarly, only mass peaks which are coincident in mass number with the peaks stored in the storage areas (M2), . . . , (Mn) are extracted and taken as spectra (S2), . . . , (Sn).

The obtained spectra (S1), (S2), . . . , (Sn) are output from the display 6 as mass spectra of individual components isolated from the mixture spectrum (S).

Where data are measured in the multifunctional mode, mass spectra which produced fragmentation at another ionization voltage corresponding to the initially output accumulation spectrum (S) are processed similarly. Mass peaks producing mass chromatograms coincident in elution start time, maximum elution time, and elution end time are extracted from the stored data. Molecular ion peaks and fragment spectra of single components corresponding to the peaks are reconstructed from the extracted results. These are output from the display 6.

In the above description of Embodiment 2, mass peaks stored in the first storage area are deleted and, at the same time, the deleted mass peaks are stored in a batch in the second storage area. Note that this simply illustrates the apparent operation but does not always mean that the mass peaks are shifted from the first storage area to the second storage area in practice. Obviously, a method can also be adopted which consists of tagging mass peaks producing mass chromatograms having the same features with a common mark and combining the mass peaks into a group such that they can be discriminated from other mass peaks.

The method and apparatus for mass spectrometry according to the present invention can be widely applied to chromatograph-mass spectrometer systems.

Having thus described our invention with the detail and particularity required by the Patent Laws, what is desired protected by Letters Patent is set forth in the following claims.

The invention claimed is:

1. A method of mass spectrometry comprising the steps of:
   separating a mixture into components by a chromatograph;
   ionizing the separated mixture components and obtaining measurement data from a mass spectrometer;
   producing a mass chromatogram from the obtained measurement data for a given period;
   extracting a spectrum from the mass chromatogram; and
   searching a library holding information about molecular structures of known compounds to thereby perform a qualitative or quantitative analysis of a compound,
   wherein a total ion chromatogram is obtained from the mass spectrometer,
   wherein an accumulation mass spectrum close to desired peak tops is extracted from the total ion chromatogram and displayed,
   wherein a desired mass peak is selected from the displayed accumulation mass spectrum, and
   wherein another mass chromatogram which is coincident in elution start time, maximum elution time, and elution end time with the mass chromatogram of the selected mass peak is selected out as a mass peak, whereby a mass spectrum of a single component is reconstructed.

2. A method of mass spectrometry as set forth in claim 1, wherein determination of the elution start time from the chromatograph, maximum elution time, and elution end time is done by fitting of a curve of a given function to the time variation of the mass chromatogram.

3. A method of mass spectrometry as set forth in claim 2, wherein the curve of the given function is a curve of a higher-order function or Gaussian function.

4. A method of mass spectrometry as set forth in claim 1, wherein said chromatograph is a liquid chromatograph.

5. A method of mass spectrometry as set forth in claim 1, wherein said mixture is a peptide mixture obtained by enzymatic digestion of a protein.

6. A mass spectrometry apparatus for reconstructing each molecular ion peak and a fragment spectrum of a single component corresponding to the peak by applying a method of mass spectrometry as set forth in claim 1 to plural mass chromatograms measured in a multifunctional mode under different mass spectrometry conditions.

7. A method of mass spectrometry for performing a qualitative or quantitative analysis of a compound by isolating a mixture into components by a chromatograph, ionizing the mixture components, obtaining measurement data from a mass spectrometer for a given period, storing the obtained measurement data in a storage device, extracting a spectrum from the stored mass chromatogram, and searching a library holding information about molecular structures of known compounds,
   wherein mass peaks producing chromatograms which are coincident in waveform with the mass chromatogram of a mass peak having a given peak intensity are found from a storage area holding all detected mass spectrograms and taken as a chromatogram group and this operation is repeated to isolate and reconstruct each molecular ion peak and a fragment spectrum of a single component corresponding to the peak.

8. A method of mass spectrometry as set forth in claim 7, wherein the mass peak having said given peak intensity is a mass peak having the highest intensity out of mass peaks not yet contained in the group.

9. A method of mass spectrometry as set forth in claim 7, wherein the decision as to whether the chromatogram is coincident in waveform with the mass chromatogram of a mass peak having a given peak intensity is made by comparisons in terms of elution start time from the chromatograph, maximum elution time, and elution end time.

10. A method of mass spectrometry as set forth in claim 9, wherein determination of the elution start time from the chromatograph, maximum elution time, and elution end time is done by fitting of a curve of a given function to the time variation of the mass chromatogram.

11. A method of mass spectrometry as set forth in claim 10, wherein the curve of said given function is a curve of a higher-order function or a Gaussian function.

12. A method of mass spectrometry as set forth in claim 7, wherein said chromatograph is a liquid chromatograph.

13. A method of mass spectrometry as set forth in claim 7, wherein said mixture is a peptide mixture obtained by enzymatic digestion of a protein.

14. A mass spectrometry apparatus for performing a qualitative or quantitative analysis of a compound by isolating a mixture into components by a chromatograph, ionizing the mixture components, obtaining measurement data from a mass spectrometer for a given period, producing a mass chromatogram from the obtained measurement data, storing the obtained measurement data in a storage device, extracting a spectrum from the mass chromatogram, and searching a library holding information about molecular structures of known compounds, said mass spectrometry apparatus comprising:
   display means for displaying an accumulation mass spectrum close to a desired peak top from a total ion chromatogram gained by the mass spectrometer;
   selection means for selecting a desired mass peak from the displayed accumulation mass spectrum; and
   reconstruction means for reconstructing a mass spectrum of a single component by extracting another mass chromatogram that is coincident in elution start time, maximum elution time, and elution end time with the mass chromatogram of the selected mass peak and selecting out the extracted mass chromatogram as a mass peak.

15. A mass spectrometry apparatus as set forth in claim 14, wherein determination of the elution start time from the chromatograph, maximum elution time, and elution end time is done by fitting of a curve of a given function to the time variation of the mass chromatogram.

16. A mass spectrometry apparatus as set forth in claim 15, wherein the curve of said given function is a curve of a higher-order function or Gaussian function.

17. A mass spectrometry apparatus as set forth in claim 14, wherein said chromatograph is a liquid chromatograph.

18. A mass spectrometry apparatus as set forth in claim 14, wherein said mixture is a peptide mixture obtained by enzymatic digestion of a protein.

* * * * *